US008505269B2

(12) United States Patent
Kobayashi et al.

(10) Patent No.: US 8,505,269 B2
(45) Date of Patent: Aug. 13, 2013

(54) METHOD, APPARATUS AND SYSTEM OF ELIMINATING STATIC CHARGE AND FILLING AND STERILIZING RESIN VESSEL

(75) Inventors: Toshiya Kobayashi, Tokyo (JP); Mitsuomi Narita, Tokyo (JP); Tomohiko Sugimori, Tokyo (JP); Tsunehiko Yokoi, Kumamoto (JP); Yukinobu Nishino, Kanazawa (JP); Masami Hayashi, Kanazawa (JP); Takashi Kadoya, Kanazawa (JP); Tokuo Nishi, Kanazawa (JP); Yukihiro Yamamoto, Kanazawa (JP); Takuya Onishi, Kanazawa (JP); Takahiro Kida, Kanazawa (JP); Kouichi Murata, Kanazawa (JP)

(73) Assignee: Shibuya Kogyo Co., Ltd., Kanazawa-shi, Ishikawa (JP)

( * ) Notice: Subject to any disclaimer, the term of this patent is extended or adjusted under 35 U.S.C. 154(b) by 333 days.

(21) Appl. No.: 12/803,276

(22) Filed: Jun. 23, 2010

(65) Prior Publication Data
US 2010/0326563 A1    Dec. 30, 2010

(30) Foreign Application Priority Data
Jun. 30, 2009    (JP) .................................. 2009-156096

(51) Int. Cl.
*B65B 3/04*    (2006.01)
(52) U.S. Cl.
USPC ................ 53/426; 53/467; 53/485; 53/111 R; 53/281
(58) Field of Classification Search
USPC ................... 53/425, 426, 467, 471, 473, 485, 53/111 R, 281
See application file for complete search history.

(56) References Cited

U.S. PATENT DOCUMENTS

| | | | | | |
|---|---|---|---|---|---|
| 3,768,227 | A | * | 10/1973 | Grisell | 53/449 |
| 4,415,085 | A | * | 11/1983 | Clarke et al. | 206/526 |
| 4,707,414 | A | * | 11/1987 | Long et al. | 428/511 |
| 4,991,379 | A | * | 2/1991 | Boeckmann | 53/552 |
| 5,014,849 | A | * | 5/1991 | Becker | 206/714 |
| 5,199,246 | A | * | 4/1993 | Rodrigo | 53/449 |
| 5,671,591 | A | * | 9/1997 | Fleenor | 53/452 |
| 5,794,412 | A | * | 8/1998 | Ronconi | 53/466 |
| 5,884,455 | A | * | 3/1999 | Draghetti et al. | 53/466 |
| 6,014,852 | A | * | 1/2000 | Weder et al. | 53/465 |
| 7,222,470 | B2 | * | 5/2007 | Ribi | 53/141 |
| 7,739,859 | B2 | * | 6/2010 | Colato et al. | 53/426 |
| 7,832,185 | B2 | * | 11/2010 | Mastio et al. | 53/426 |
| 8,117,803 | B2 | * | 2/2012 | Nishino et al. | 53/167 |
| 8,132,598 | B2 | * | 3/2012 | Mastio et al. | 141/51 |
| 2006/0086066 | A1 | * | 4/2006 | Heinz | 53/428 |
| 2009/0017747 | A1 | * | 1/2009 | Wu et al. | 454/189 |
| 2009/0045350 | A1 | * | 2/2009 | Humele et al. | 250/455.11 |
| 2010/0095639 | A1 | * | 4/2010 | Hohenhorst et al. | 53/452 |
| 2011/0100401 | A1 | * | 5/2011 | Fiorentini | 134/22.12 |

FOREIGN PATENT DOCUMENTS

| | | |
|---|---|---|
| JP | 2006-216453 | 8/2006 |
| JP | 2009-051517 | 3/2009 |

* cited by examiner

*Primary Examiner* — Hemant M Desai
(74) *Attorney, Agent, or Firm* — Flynn, Thiel, Boutell & Tanis, P.C.

(57) ABSTRACT

Charges accumulated inside a wall structure of a resin vessel, which is sterilized by an electron beam irradiator, and an ionizer disposed outside a filler emits to the outer surface of the resin vessel are eliminated with negative ions having the same polarity as that of charges accumulated in the wall section of the resin vessel, while conveying the resin vessel sterilized by the electron beam irradiator to the filler, by which liquid fills the resin vessel.

8 Claims, 5 Drawing Sheets

METHOD, APPARATUS AND SYSTEM OF ELIMINATING STATIC CHARGE AND FILLING AND STERILIZING RESIN VESSEL

BACKGROUND OF THE INVENTION AND RELATED STATEMENT THEREOF

The present invention relates to a static charge elimination method for eliminating static charges inside a wall structure of a resin vessel, a sterilization and filling method for a resin vessel for eliminating charges inside a wall structure of a resin vessel during a sterilization process of the resin vessel, a filling and capping method for a resin vessel, a static charge elimination apparatus for a resin vessel, and a sterilization and filling system for a resin vessel.

In a conventional technology, there has been widely known an electron beam sterilization apparatus for sterilizing a resin vessel such as a PET bottle by being irradiated with an electron beam. It has also conventionally known that the resin vessel becomes charged when being irradiated with the electron beam. In such a case, dust and dirt are attracted to the charged resin vessel, which may cause an undesirable matter. Then, there have been provided several apparatus for eliminating static charge from a charged resin vessel (for example, refer to Japanese Patent Application Laid-open Publication Nos. 2006-216453 and 2009-51517: Patent Documents 1 and 2).

The above Patent Document 1 discloses an invention concerning a static charge elimination apparatus. This static charge elimination apparatus is provided with a hollow ionizing chamber, in which a flow-in port through which air or unreactive gas is introduced is formed at an upper central portion in this ionizing chamber, and a flow-out port is also formed at a lower central portion thereof in a fashion opposed to the flow-in port.

Moreover, on the side portion of the ionizing chamber, a soft X-ray generating portion of a soft X-ray generator is positioned, and a soft X-ray generated through the soft X-ray generating portion is radiated into the ionizing chamber through a soft X-ray irradiating window formed in the side surface portion of the ionizing chamber. The soft X-ray radiated into the ionizing chamber acts to ionize the air or unreactive gas to thereby generate positive or negative ions.

Furthermore, a back electrode (i.e., back plate) is disposed on an inner surface of the ionizing chamber, and a filter electrode, having a perforated plate shape, is also disposed at a front (tip) end portion of the flow-out port. In addition, a plate-shaped induction electrode is mounted to the lower portion of the ionizing chamber on the same level as the back plate and the filter electrode. Power sources for generating alternating current are connected to the back electrode, the filter electrode and the induction electrode so that the polarities of the voltages applied to these electrodes are switched alternately.

The static elimination apparatus disclosed in the above Patent Document 1 is disposed above a resin film, which is an object from which static charge is eliminated, air or unreactive gas is introduced into the ionizing chamber through the flow-in port, and the soft X-ray is emitted through the soft X-ray irradiating window, thus generating positive and negative ions in the ionizing chamber.

Then, the back electrode, the filter electrode and the induction electrode are applied with the voltage having the same polarity by the alternating current sources, whereby, in the ionizing chamber, ions having the same polarity as that of the applied voltage (unipolar ions) are generated, and on the other hand, by the filter electrode and the induction electrode disposed in opposition to the resin film, on the surface of the resin film, a charge having a polarity reverse to that of the applied voltage is induced.

As mentioned above, the charge induced on the surface of the resin film and charge originally existing thereon are neutralized by blowing the unipolar ions generated in the ionizing chamber. The charge induced on the surface of the resin film and the polarities of the unipolar ions generated in the ionizing chamber are alternately switched in positive or negative state by alternately switching, in positive or negative state, the polarities of the voltages to be applied by the alternating current power source, and as a result of the repetition of these operations, the charges inside the resin film can be surely eliminated.

Furthermore, the Patent Document 2 discloses a method of manufacturing a vessel with an inner content capable of suppressing the charging of a vessel body. In this manufacturing method, a lid is mounted to a neck portion near a mouth of the vessel body before sealing, and the vessel body is arranged in a conveyance holder in a state in which the lid is directed downward. A seal portion disposed on a side reverse to the vessel lid is opened, and an inner content filling nozzle is inserted into the vessel from the upper side of the opening before the sealing of the same and fills the vessel with the inner content such as liquid.

When a predetermined amount of the inner content fills the vessel, the filling is stopped and the filling nozzle is pulled upward outside the vessel body. Thereafter, a conducting member or material is inserted inside the vessel body so as to contact the inner content to thereby eliminate the static charge of the vessel body through the inner content and the conducting member or material.

Furthermore, in another conventional technology, there is also disclosed a method in which a filling nozzle and a conducting member are inserted into the vessel body from the upper side thereof before the sealing of the same, and the conducting member is contacted to the inner content while filling the inner content through the filling nozzle to thereby eliminate the static charges of the vessel body through the inner content and the conducting member.

It is however found that it is difficult to completely eliminate charges charged inside a resin vessel (in the interior of a resin material forming the vessel) by the structure in which the ions are blown on an object subjected to the static charge elimination disclosed in the above Patent Document 1 and by the structure in which a conducting member or material is inserted into an inner content to fill a resin vessel as in a method of manufacturing a resin vessel in which the inner content fills the resin vessel as disclosed in the above Patent Document 2, thus being inconvenient.

OBJECT AND SUMMARY OF THE INVENTION

Therefore, an object of the present invention is to eliminate charges charged inside a wall structure of a resin vessel sterilized by being irradiated with an electron beam.

This object can be achieved by the invention of a method of eliminating static charge from a resin vessel by using an apparatus including a liquid supply unit for supplying a liquid into a resin vessel and a charge applying unit for applying a charge to an outer surface of the resin vessel, wherein, by applying a charge having the same polarity as that of the charge remaining in an interior of a wall section of the resin vessel, while supplying the liquid into the resin vessel, an ion-carrying charge having a polarity reverse to that of the charge remaining in an interior of the wall section of the resin vessel is attracted to an inner surface of the resin vessel.

The above object can be also achieved by the invention of a method of sterilizing and filling a resin vessel including a sterilizing process for sterilizing a resin vessel by being irradiated with an electron beam and a filling process for filling the resin vessel with a liquid, wherein a filling nozzle for filling the resin vessel with the liquid and a negative charge applying unit for applying negative charge on an outer surface of the resin vessel are provided, and during the liquid filling process into the resin vessel, the negative charge is applied to the outer surface of the resin vessel.

The above object can be also achieved by the invention of a resin vessel filling and capping method including a sterilizing process for sterilizing a resin vessel by being irradiated with an electron beam, a filling process for filling a liquid into the resin vessel and a capping process for applying a cap to the resin vessel after completion of the liquid filling, wherein a conductive member to be inserted into the resin vessel and a negative charge applying unit for applying negative charge onto an outer surface of the resin vessel are provided, and during a period between the filling process and the capping process, the conductive member is contacted to the liquid filled into the resin vessel and the negative charge is applied to the outer surface of the resin vessel by the negative charge applying unit, and after the negative charge application, a cap is applied to the resin vessel.

The above object can be also achieved by the invention of a resin vessel filling and capping method including a sterilizing process for sterilizing a resin vessel by being irradiated with an electron beam, a filling process for filling a liquid into the resin vessel and a capping process for applying a cap to the resin vessel after completion of the liquid filling, wherein a conductive member to be inserted into the resin vessel and a negative charge applying unit for applying a negative charge onto an outer surface of the resin vessel are provided, and during a period between the filling process and the capping process, the negative charge is applied to the outer surface of the resin vessel by the negative charge applying unit to apply the negative charge application, the conductive member is contacted to the liquid filled into the resin vessel, and a cap is thereafter applied to the resin vessel.

The above object can be also achieved by the invention of an apparatus for eliminating static charge from a resin vessel including a liquid supply unit for supplying a liquid into a resin vessel and a charge applying unit for applying charge to an outer surface of the resin vessel which is filled with the liquid by the liquid supply unit, wherein a charge having a same polarity as that of a charge remaining in an interior of a wall section of the resin vessel is applied to the outer surface of the resin vessel by the charge applying unit during the supply of the liquid into the resin vessel by the liquid supply unit.

The above object can be also achieved by the invention of a resin vessel sterilizing and filling system, comprising: an electron beam irradiator for irradiating a resin vessel, which is being conveyed, with an electron beam and sterilizing the resin vessel; a filling unit having a filling nozzle through which a liquid is discharged into the resin vessel from an upper portion of a mouth portion of the resin vessel irradiated with the electron beam; a capping unit for applying a cap to the resin vessel which is filled up with the liquid; and a negative charge applying unit for applying a negative charge onto an outer surface of the resin vessel which is filled up with the liquid by the filling unit, wherein during the liquid filling process into the resin vessel by the filling unit, a negative charge is applied to the outer surface of the resin vessel by the negative charge applying unit, and thereafter, a capping process is performed by the capping unit.

The object can be also achieved by the invention of a resin vessel sterilizing and filling system comprising: an electron beam irradiator for irradiating a resin vessel, which is being conveyed, with an electron beam and sterilizing the resin vessel; a filling unit for filling the resin vessel, irradiated with the electron beam, with a liquid; a capping unit for applying a cap to the resin vessel which is filled up with the liquid; a conductive member inserting unit provided for a conveyance path between the filling unit and the capping unit and adapted for inserting a conductive member into the resin vessel; and a negative charge applying unit for applying a negative charge onto an outer surface of the resin vessel which is filled up with the liquid by the filling unit, wherein a capping process is performed by the capping unit after the negative charge is applied by the negative charge applying unit to the outer surface of the resin vessel while contacting the conductive member to the liquid filled into the resin vessel between the filling unit and the capping unit.

The above object can be also achieved by the invention of a resin vessel sterilizing and filling system comprising: an electron beam irradiator for irradiating a resin vessel, which is being conveyed, with an electron beam and sterilizing the resin vessel; a filling unit for filling the resin vessel, irradiated with the electron beam, with a liquid; a capping unit for applying a cap to the resin vessel, which is filled up with the liquid; a conductive member inserting unit provided for a conveyance path between the filling unit and the capping unit and adapted for inserting a conductive member into the resin vessel; and a negative charge applying unit for applying a negative charge onto an outer surface of the resin vessel into which the conductive member is inserted, wherein a capping process is performed by the capping unit after the negative charge is applied by the negative charge applying unit to the outer surface of the resin vessel while contacting the conductive member to the liquid filled into the resin vessel between the filling unit and the capping unit.

In the above respective inventions, the above object may be also achieved by constructing the charge applying unit so as to have a structure capable of emitting to the outer surface of the resin vessel with the ions.

As described above, according to the invention, since the ion carrying charge having a polarity reverse to that of the charge remaining in an interior of the wall section of the resin vessel is attracted to an inner surface of the resin vessel, while supplying the liquid into the resin vessel, by applying a charge having the same polarity as that of the charge remaining in an interior of a wall section of the resin vessel, the charges charged inside the wall structure of the resin vessel can be effectively eliminated.

Furthermore, according to the inventions concerning the resin vessel sterilizing method and the resin vessel filling method, as like as the method of eliminating static charge from the resin vessel, the charges charged inside the wall structure of the resin vessel can be effectively eliminated.

DETAILED DESCRIPTION OF THE PREFERRED EMBODIMENT

Hereunder, the present invention will be described with reference to preferred embodiments represented by the accompanying drawings.

Figure 1:
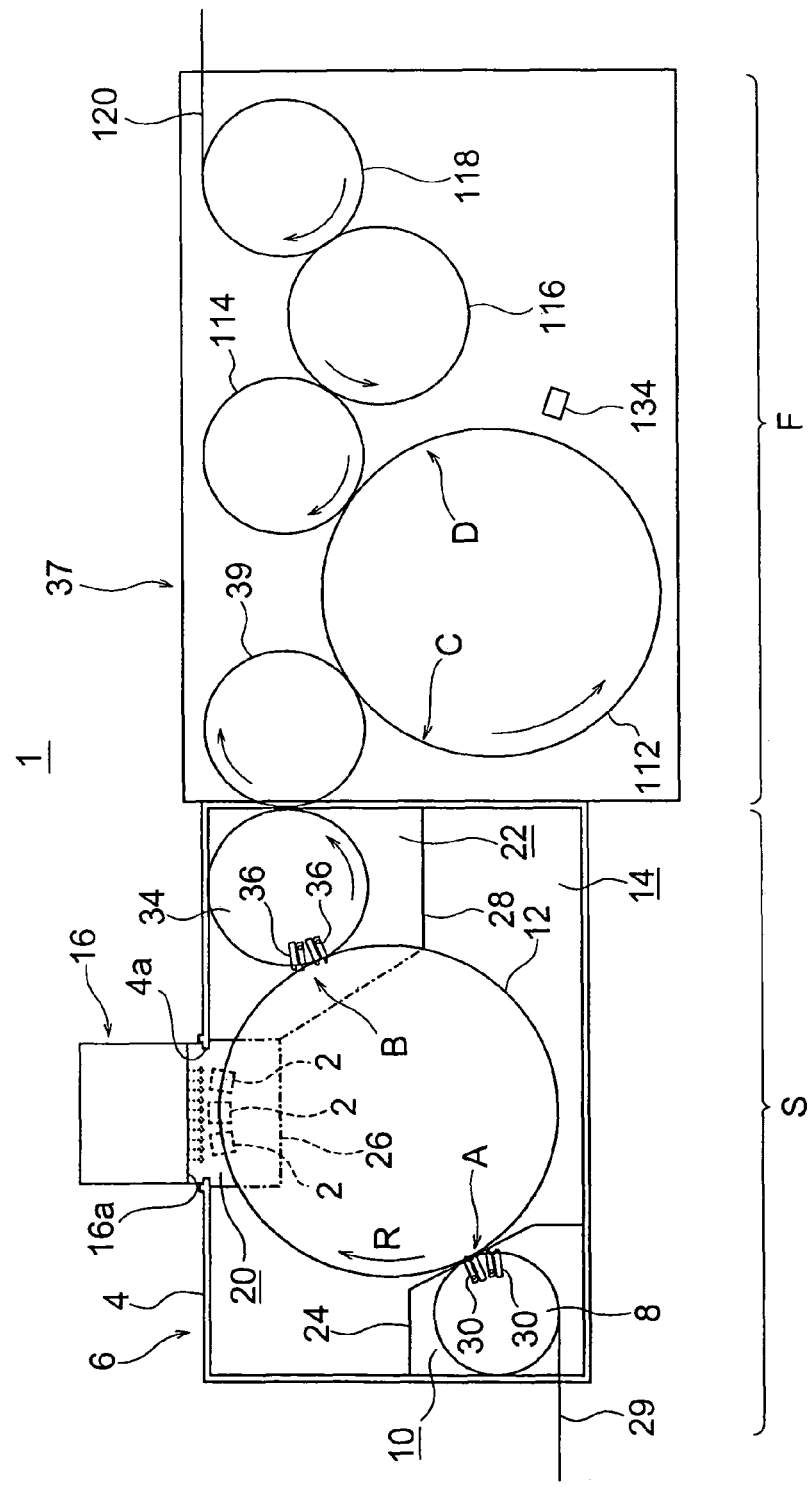
FIG. 1 is an illustrated plan view showing an entire structure of a sterilizing and filling apparatus for carrying out a method of eliminating static charge of a resin vessel and a method of sterilizing and filling a resin vessel according to one embodiment of the present invention.

FIG. 1 shows a sterilizing and filling apparatus (entirely denoted by reference numeral "1") for a resin vessel in which liquid is filled as an inner content and is then capped to seal the resin vessel after the sterilization.

With reference to FIG. 1, a left side represents a sterilizing zone S and a right side represents a filling and capping zone F, which may be merely called "filling zone" for the sake of convenience. In the sterilizing zone S, there is provided a sterilization chamber 6 surrounded by a wall structure 4 made of lead for shielding electron beam or X-ray (braking X-ray) from leaking outside at a time when a resin vessel 2 is irradiated with the electron beam to sterilize the vessel 2.

Within this sterilization chamber 6, there are provided an inlet side carry-in chamber section 10, a main chamber section 14, an irradiation chamber section 20 and a carry-out chamber section 22.

In the carry-in chamber section 10, a carry-in wheel 8 is disposed, and in the main chamber section 14, there is disposed a conveyance wheel 12 which rotates and conveys the resin vessel 2 transferred from the carry-in wheel 8. The irradiation chamber section 20 is disposed on the front side of an electron beam irradiator 16, and in this irradiation chamber section 20, the resin vessel 2 is conveyed in a state of being held by a bottle support unit 18 (see FIG. 2) mounted to the carry-in wheel 12. The carry-out chamber section 22 is formed continuously to an outlet side (right side in FIG. 1) of the irradiation chamber section 20 and adapted to convey the resin vessel 2, which was sterilized by the electron beam irradiation, to the downstream side (i.e., filling zone F) of a vessel conveyance path or route while maintaining aseptic condition of the sterilized vessel 2. These chamber sections 10, 14, 20 and 22 are defined by partition walls or plates 24, 26 and 28 within the sterilization chamber 6. Furthermore, these wall sections 4 and the partition walls 24, 26 and 28 are formed with holes or openings, not shown, allowing the resin vessel 2 to pass through for transferring of the resin vessel 2, respectively.

The vessel 2 which is sterilized in the sterilizing zone S and filled up with an inner content such as liquid in the downstream-side filling zone F is made of a resin, such as PET, bottle, has a shank (body) portion substantially rectangular in cross section (as schematically shown in FIG. 1) and has an upper cylindrical mouth portion 2a as shown in FIG. 2A. Furthermore, a flange portion 2b is formed to a lower side of the cylindrical mouth portion 2a, and the resin vessel 2 is conveyed in a suspended state such that a portion above or below the flange portion 2b is held by a gripper or a lower surface side of the flange portion 2b is held by a bottle support unit 18 or other support unit or member.

The resin vessel 2 is continuously conveyed by an air conveyer 29 and separated one by one at a predetermined interval by an infeed screw, not shown, and thereafter, the respective resin vessel 2 is carried inside the carry-in chamber section 10 disposed on the inlet side of the sterilization chamber 6.

The carry-in wheel 8 disposed within the carry-in chamber section 10 is provided with a plurality of grippers 30 arranged at an equal interval in a circumferential direction thereof, and each gripper 30 grips a portion above the flange portion 2b of the resin vessel 2 and conveys the resin vessel 2 in the gripped state. The resin vessel 2 held by the grippers 30 of the carry-in wheel 8 and conveyed while being rotated are transferred to the conveyance wheel 12 arranged inside the main chamber section 14.

A plurality of bottle support units 18 are mounted to the conveyance wheel 12 arranged inside the main chamber section 14 at an equal interval in the circumferential direction thereof (see FIG. 2A), and each of these bottle support units 18 supports the lower surface side of the flange portion 2b of each resin vessel 2 and convey the resin vessel 2 in this state.

The carry-in wheel 8 and the conveyance wheel 12 are rotated synchronously, and each of the resin vessels 2 is transferred to each of the bottle support units 18 at the vessel transferring position "A" from the gripper 30 of the carry-in wheel 8.

The resin vessels 2 are rotated and conveyed in the state supported by the respective bottle support units 18 of the conveyance wheel 12. Continuously, the resin vessels 2 pass inside the irradiation chamber section 20, and during the passing through the irradiation chamber section 20, the resin vessel 2 is irradiated along the vertically entire longitudinal direction with the electron beam emitted from the electron beam irradiator 16, thereby being sterilized. Thus the sterilized resin vessel 2 is guided into the carry-out chamber section 22 continuously arranged to the irradiation chamber section 20 and then transferred to the carry-out wheel 34.

The carry-out wheel 34 is provided with a plurality of grippers 36 on the peripheral portion thereof at an equal interval in the circumferential direction, and each of the grippers 36 receives each of the resin vessels 2 supported by each of the bottle support units 18 of the conveyance wheel 12 by gripping and holding the portion above the flange portion 2b of the resin vessel 2. This carry-out wheel 34 is also synchronously rotated with the conveyance wheel 12, and at the transferring position "B", the resin vessel 2 is transferred to each gripper 36 of the carry-out wheel 34 from the bottle support unit 18 of the conveyance wheel 12.

The resin vessel 2 held by the gripper 36 of the carry-out wheel 34 is then transferred to a vessel support unit, not shown, of a support wheel 39 arranged on an inlet side of a succeeding chamber (i.e., chamber 37 in the filling zone F) to be thereby subjected to a next process.

The sterilization chamber 6 has an opening 4a formed in the lead wall section (structure) 4 at the portion where the irradiation chamber section 20 is formed, and the electron beam irradiator 16 is mounted to this opening 4a. This electron beam irradiator 16 is provided with a vacuum chamber (acceleration chamber), not shown, for irradiating the resin vessel 2 with the electron beam, and as is known, a filament is heated in an evacuated atmosphere in the vacuum chamber to thereby generate thermal electrons, which are then accelerated by applying a high voltage to create a high speed electron beam. Thereafter, the electron beam is taken out into the atmosphere through a metal foil such as titanium(Ti) attached to an irradiation window 16a of the electron beam irradiator 16, and the taken-out electron beam is thereafter irradiated onto an object to be treated (herein, resin vessel 2) to perform the sterilization thereof. Further, though not shown in FIG. 1, a beam collector 38 (as shown in FIG. 2A) is disposed on a back side of the resin vessel 2 irradiated with the electron beam generated from the electron beam irradiator 16.

Hereunder, with reference to FIGS. 2A and 2B, the structures of each of the bottle support units 18 provided for the conveyance wheel 12 and an earth electrode to be inserted into the resin vessel 2 at the sterilization process will be briefly described.

The conveyance wheel 12 is provided with a plate 40 having a horizontal disc-shape, an annular rotary plate 41 fixed to the outer periphery of the disc-shaped plate 40, and an annular intermediate plate 42 disposed above the rotary plate 41 to be integrally rotatable therewith. A plurality of cylindrical rotating shafts 44 extending perpendicularly are supported to be rotatable to outer peripheral portions of the rotary plate 41 and the intermediate plate 42 through ball bearings 46 and 48, respectively, each at an equal interval in the circumferential directions thereof.

A horizontal mount member 50 is fixed to the lower end portion of these cylindrical rotating shafts 44. A pair of grip members 52A and 52B (which are arranged on the front and rear sides of the drawing paper of FIG. 2A) are provided on the lower side of the mount member 50 so as to hold the resin vessel 2 at the directly lower positions of the cylindrical rotating shafts 44, respectively.

Further, the bottle support unit 18 has a structure substantially the same as a bottle support unit 18 disclosed in the Japanese Patent Application No. 2008-280304 (the detail of which is omitted herein), and the grip members 52A and 52B are attached to lower end portions of a pair of plate springs 54A and 54B so that the resin vessel 2 are held by the spring forces of these plate springs 54A and 54B.

A pinion gear 64 is fixed to an upper (top) end portion of each of the cylindrical rotating shafts 44, to which the bottle support unit 18 is mounted, to be projected above the intermediate plate 42. Furthermore, the cylindrical rotating shaft 44 is supported by both of the annular rotary plate 41 and the annular intermediate plate 42 respectively fixed to the outer periphery of the disc-shaped plate 40. An intermediate shaft 66 extending vertically is rotatably supported by ball bearings 68 and 70 to both of the plates 41, 42 at the position radially inward of the cylindrical shaft 44.

Further, sector gear 72 is mounted to the upper end portions of the respective intermediate shafts 66 at substantially the same height level as that of the pinion gear 64 of the rotating shafts 44, respectively. Teeth are formed at radially outward surface portion of the conveyance wheel 12, the teeth being meshed with the pinion gears 64.

On the other hand, a vertical pin 74 is attached to the end portion of the sector gear 72 directed radially inward of the conveyance wheel 12, that is, the left side end in FIG. 2A, and a cam follower 76 is supported at the upper end portion of the vertical pin 74 to be rotatable.

Furthermore, a tension coil spring 80 is interposed between the lower end portion of the vertical pin 74 and a spring receiving pin 78 fixed to an inner peripheral end of the intermediate plate 42 so as to attract the end portion of the sector gear 72 toward the radially inward direction of the conveyance wheel 12.

Above the disc-shaped plate 40 of the conveyance wheel 12, there is disposed a circular fixed plate 82, which does not rotate or is not rotated, and a rotational cam 84 for swinging the sector gear 72 is fixed to the outer peripheral portion of the fixed plate 82. The outer peripheral surface of the cam 84 is formed as a cam surface, along which the cam follower 76 is moved while being rotated. According to the swinging motion of the sector gear 72 in the radial direction in accordance with the rotating movement of the cam follower 76, the sector gear 72 is rotated around the intermediate shaft 66 to thereby rotate the pinion gear 64.

Each of the bottle support units 18 is mounted to the lower end portion of the cylindrical rotating shaft 44, to the upper end of which the pinion gear 72 is fixed, and according to the swinging motion of the sector gear 72, the pinion gear 64 is rotated, and the cylindrical rotating shaft 44 disposed above the mouth portion of the resin vessel 2 is rotated, thereby rotating the resin vessel 2, now being conveyed in the state supported by the bottle support unit 18, around the central axis thereof. The above operations will be performed with respect to the respective bottle support units 18 and their associated members or units.

According to the embodiment mentioned above, the pinion gears 64 are rotated by the pivotal motions of the sector gear 72, and the resin vessel 2 is thereby rotated by about 180 degrees in the positive and reverse directions.

The horizontal mount member 50 mentioned hereinbefore is formed with a through hole 50a at a portion vertically according with an inner hole 44a of the cylindrical rotating shaft 44. A top surface and the outer peripheral surface of the conveyance wheel 12 are covered with a cover 88. This cover 88 is composed of a metal material having conductivity. Furthermore, the upper portion of the pinion gear 64 reaches the cover 88 covering the top portion extending upward, and a space between it and the cover 88 is sealed to be swingable. According to such a structure, the circular hole 44a of the rotating shaft 44 and the circular hole 64a of the pinion gear 64 fixed to the upper end portion of the rotating shaft 44 vertically penetrate the inner space defined by the disc-shaped plate 40 and the cover 88, so that an ambient environment is maintained in the aseptic condition and an inner environment surrounded by the disc-shaped plate 40 and the cover 88 are shut off therebetween.

The conveyance wheel 12 is provided with the earth electrode 90, which is inserted into the resin vessel 2 at the time of irradiating the resin vessel 2 with the electron beam. The earth electrode 90 is attached to the lower end of a support rod 92 standing vertically, and these earth electrode 90 and the support rod 92 are disposed so as to be vertically movable through the circular holes 44a and 64a of the cylindrical rotating shaft 44 and the pinion gear 64 and the through hole 50a formed to the horizontal mount member 50 disposed on the lower side thereof.

Figure 2:
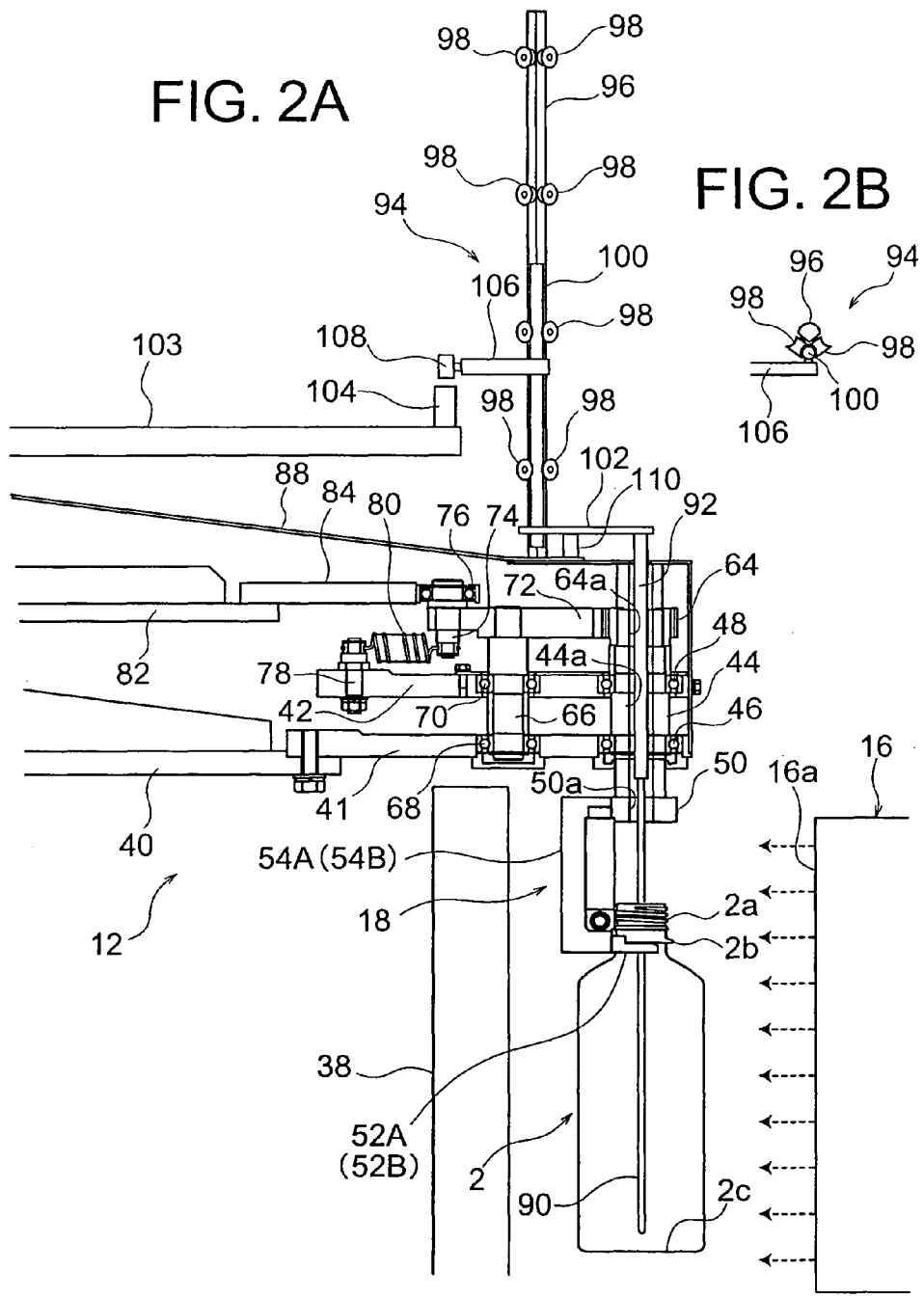
FIGS. 2A and 2B are respectively an illustrated vertical sectional view of an essential portion of an electron beam sterilization apparatus provided for the sterilizing and filling apparatus.

A mechanism for vertically moving each of the earth electrodes 90 will be described hereunder with reference to FIG. 2.

The mechanism includes a vertically standing guide mechanism 94 disposed above the cover 88 inward the position at which the cylindrical rotating shaft 44 is arranged. This guide mechanism 94 is provided with, as shown in FIGS. 2A and 2B, an upright guide member 96 and a plurality guide rollers 98 attached to vertical plural portions of the guide member 96. The guide rollers 98 are arranged at vertically appropriate portions of the guide member 96 respectively in pairs, and an elevating rod 100 is disposed to be vertically movable in a state supported by the guide rollers 98 and the guide member 96. To the lower end portion of the elevating rod 100, there are mounted the support rod 92 and the earth electrode 90 through a horizontal mount member 102 so that the earth electrode 90 is vertically movable by the elevating motion of the elevating rod 100.

Further, the earth electrode 90 may be made of a metal such as stainless, aluminum, titanium and the like, or other electrically conductive material. Furthermore, the earth electrode 90 may have various shapes, such as round-rod shape, having square, rectangular or polygonal section. Further, the outer peripheral surface of the earth electrode 90 may be formed with a plurality of projections so as to provide saw-teeth shape or may be provided with a brush to easily induce charges.

A horizontal steady member 103 is disposed, independently from the conveyance wheel 12, above the top surface of the cover 88, and an elevating cam 104 is attached to the outer peripheral portion of the steady member 103. Furthermore, an elevating (liftable) member 106 is fixed to the elevating rod 100 at a position higher than the location of the mount member 102, and a cam follower 108 is mounted to an end portion of the elevating member 106. This cam follower 108 moves while rotating on the upper surface (cam surface) of the elevating cam 104 to be moved up and down in accordance with the cam shape of the elevating cam 104 to thereby moving up and down the earth electrode 90.

When the cam follower 108 is pushed upward by the elevating cam 104 to the most upward position, the lower end of the earth electrode 90 takes a position above the mouth portion 2a of the resin vessel 2, and on the other hand, when it is lowered to the most downward position, the lower end of the earth electrode 90 is inserted into the resin vessel 2 to a position near the inner bottom surface 2c thereof as shown in FIG. 2A.

It is further to be noted that, at this operation, the lowering motion of the lower end of the elevating rod 100 is restricted by abutment of the horizontal mount member 102 against the support member 110 fixed to the top surface of the cover 88, and at this time, the cam follower 108 stops at a height level at which the cam follower 108 does not contact the cam surface of the elevating cam 104. Under this state, the earth electrode 90 becomes conductive to the cover 88 which is made of a metal conductive material through the support rod 92, the mount member 102 and the support member 110, thus creating the conductive state between the earth electrode 90 and the cover 88 and flowing the electric charge from the earth electrode 90 to the cover 88.

After the resin vessel 2 conveyed in a state of being supported by the bottle support unit 18 of the conveyance wheel 12 is irradiated with the electron beam emitted from the electron beam irradiator 16 to sterilize the resin vessel 2, the resin vessel 2 is transferred to the gripper 36 of the carry-out wheel 34 and then rotated and conveyed outward.

The filling zone F includes a chamber 37 arranged adjacent to the sterilization chamber 6 of the sterilizing zone S. The resin vessel 2 rotated and conveyed by the carry-out wheel 34 of the sterilizing zone S is transferred to a filler 112 through the supply wheel 39 arranged on an inlet (entrance) side of the chamber 37 in the filling zone F.

The resin vessel 2 transferred to the supply wheel 39 is conveyed, while being rotated, and is then transferred to the filler 112. The filler 112 receiving the resin vessel 2 from the supply wheel 39 fills the resin vessel 2 with the inner content such as a liquid during the rotation and conveyance of the resin vessel 2. The resin vessel 2 filled up with the inner content by the filler 112 is taken out by an intermediate wheel 114 which also acts as a discharge wheel of the filler 112 and a supply wheel of the capper and then supplied to the capper 116. The resin vessel 2 subjected to the capping operation by the capper 116 is taken out from capper 116 by the discharge wheel 118, and then fed for the next process by means of the discharge conveyer 120.

Figure 3:
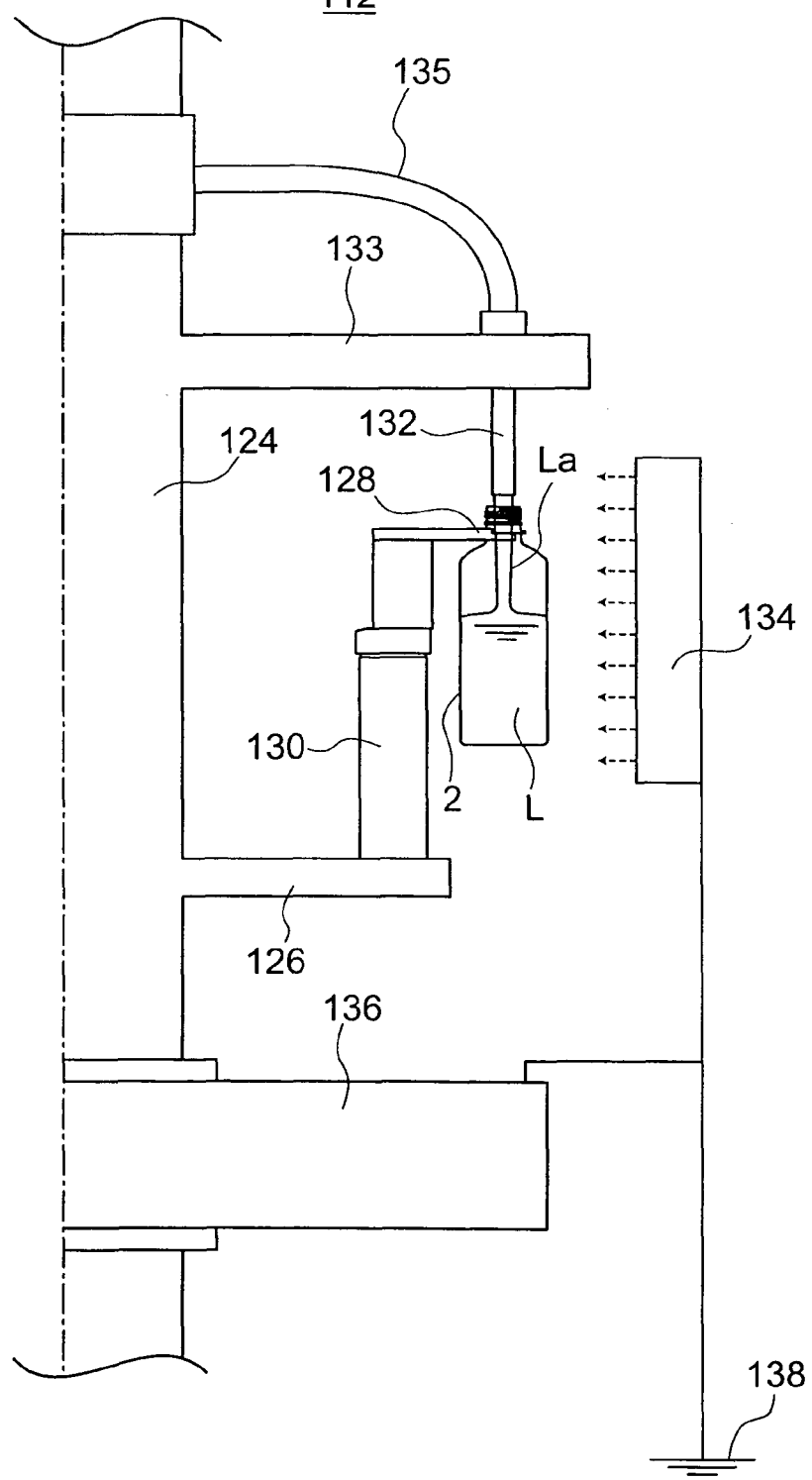
FIG. 3 is an illustrated vertical sectional view of a filler provided for the sterilizing and filling apparatus.

The filler 112 is provided, as shown in FIG. 3, with a rotary table 126 attached to a rotating shaft 124 vertically extending at the central portion of the rotation, and the rotary table 126 has an outer periphery to which grippers 128 for holding the resin vessel 2 is arranged at an equal interval in the circumferential direction thereof.

Each of these grippers 128 is attached to an upright stand 130 so as to be directed radially outward, and each of the resin vessels 2 is held by each of the grippers 128 and then conveyed while being rotated. Further, filling nozzles 132 are arranged above the respective resin vessels 2 held by the grippers 128, respectively. Each of the filling nozzles 132 is attached to an outer periphery of a second rotary table 133 arranged above the rotary table (first rotary table) 126, and the resin vessel 2 held by the gripper 128 and then conveyed, while being rotated, is then fed with a conductive liquid fed through a liquid supply pipe 135. The liquid fills the resin vessel 2 from each filling nozzle 132 during the movement along a predetermined section (corresponding to a filling area from the position C to the position D in FIG. 1).

The filler 112 is provided with a superimposed voltage-type (voltage-apply-type) ionizer 134, as a static elimination device, outside the vessel conveying path or route by the gripper 128. This ionizer 134 is disposed on the outer peripheral side of a rear side of the filling process near the filling finishing position D of the filler 112, and as shown in FIG. 3, this ionizer 134 is positioned at a height level capable of emitting ions throughout the entire length of the resin vessel 2 and has a vertical length capable of achieving such an ion emission. Further, since the structure of this voltage-apply type ionizer 134 is well known, detailed explanation thereof is omitted herein. That is, it has a structure in which corona discharge is spontaneously caused to a tapered sharp electrode needle by applying a high voltage, and in this embodiment, an ionizer generating only negative ions is adopted by applying a negative high voltage.

The filling nozzle 132 is connected to an earth 138 side of the ionizer 134 through the rotating shaft 124 of the filler 112 made of a conductive metal and a base 136 supporting this rotating shaft 124, and as mentioned hereinafter, an ion route or path connecting a space between the filling nozzle 132 and the ionizer 134 is formed. Further, in this embodiment, although the position at which the ionizer 134 on the outer peripheral side of the filler 112 is disposed is provided at the rear side position near the filling finishing position D in the filling section of the filler 112, this position is not necessarily provided at this rear side position, and it may be disposed at a front half position thereof. However, it is necessary for the ionizer 134 to be disposed in areas C-D in which the filling process is performed, and it is preferred to fill the resin vessel 2 with much liquid amount.

The operation and function of the sterilizing and filling apparatus 1 of the structures mentioned above will be explained hereunder.

The resin vessel 2 to be sterilized by the sterilizing and filling apparatus according to this embodiment are conveyed by the neck conveyer 29 and separated with a predetermined pitch interval and then carried into the carry-in chamber section 10 of the aseptic chamber 6 surrounded by the outer wall sections 4 made of lead. The carry-in wheel 8 disposed within the carry-in chamber section 10 is equipped with a plurality of the grippers 30 arranged at an equal interval in the circumferential direction thereof, and the grippers 30 grip the upper side portions of the flanges 2b formed to the lower side of the cylindrical mouth portions 2a of the resin vessels 2, respectively, carried into the carry-in chamber section 10 from the outside the aseptic chamber 6.

Each of the resin vessels 2 held by the gripper 30 is rotated and conveyed by the rotation of the carry-in wheel 8, and transferred to the bottle support unit 18 provided for the conveyance wheel 12 from the gripper 30 of the carry-in wheel 8 at the bottle transferring position A.

Each of the bottle support units 18 is rotated and moved in such a manner that one of the gripping members 52A and 52B is directed forward in the rotating direction and the other one thereof is directed rearward in the rotating direction, and at the bottle transferring position A, the mouth portion 2*a* of the resin vessel 2 held by the gripper 30 of the carry-in wheel 8 is pushed into the space between the gripping members 52A and 52B. These gripping members 52A and 52B are attached to the lower end portions of the plate springs 54A and 54B, which are forcibly opened so that the mouth portion 2*a* of the resin vessel 2 is pushed into the space between both the gripping members 52A and 52B. Thereafter, both the plate springs 54A and 54B are returned to their original positions by the self-spring force, and as shown in FIG. 2A, the lower side of the flange 2*b* of the resin vessel 2 is held so that the lower surface thereof is supported as shown in FIG. 2A.

According to the rotating motion of the conveyance wheel 12, the resin vessel 2 supported by the bottle support unit 18 is rotated and conveyed in an arrowed direction R as shown in FIG. 1 and enters the electron beam irradiation chamber section 20.

When the resin vessel 2 is irradiated with the electron beam in the irradiation chamber section 20, the earth electrode 90 is lowered by the elevating cam 104, and as shown in FIG. 2A, is inserted into the resin vessel 2 so that the tip (lower) end portion thereof reaches a position of a height level near the bottom surface 2*c* of the resin vessel 2. Further, in the sections or areas other than the area in which the electron beam irradiates the resin vessel 2, the earth electrode 90 is raised upward by the elevating cam 104 so that the tip end thereof is positioned above the mouth portion 2*a* of the resin vessel 2.

As mentioned above, the resin vessel 2 into which the earth electrode 90 is inserted is irradiated with the electron beam to be thereby sterilized during the movement in front of the irradiating window 16*a* of the electron beam irradiator 16. If the electron beam irradiates the resin vessel 2 with no earth electrode 90, the resin vessel 2 is charged, but as in this embodiment, by inserting the earth electrode 90 into the resin vessel 2 at the electron beam irradiation period, the emitted electron beam passes through the resin material forming the resin vessel 2, and the electrons entering inside the resin vessel 2 through the opening of the mouth portion 2*a* are introduced by the earth electrode 90 and flow into the entire structure of the apparatus from the cover 88 through the support rod 92, the mount member 102 and the support member 110, thus suppressing the interior of the resin material forming the inner surface and the wall section of the resin vessel 2 from being charged. Especially, the electrons emitted from the electron beam irradiator 16 towards the outer surface of the resin vessel 2 act to transmit the resin material by not only the penetrating force by the acceleration at the time of electron beam irradiation but also the induction to the earth electrode 90 from the interior of the resin vessel 2, and hence, the electrons remain in the interior of the resin material, thus being suppressed from being charged.

Further, the cylindrical rotating shaft 44 to which each of the bottle support units 18 is mounted, and the pinion gear 64 fixed to the upper end thereof is meshed with the sector gear 72, which is swung by the rotational cam 84 mounted to the outer periphery of the fixing plate 82 disposed above the sector gear 72. During the movement in front of the electron beam irradiator 16 by the operation of the rotational cam 84, the cylindrical rotating shaft 44 is rotated so that the resin vessel 2 supported by the bottle support unit 18 is rotated by about 180 degrees in positive and reverse directions.

As mentioned above, by the rotation of the resin vessel 2 by about 180 degrees in front of the electron beam irradiating window 16*a* of the electron beam irradiator 16, the inner and outer surfaces of the resin vessel 2 can be irradiated with the electron beam throughout the entire longitudinal (vertical) direction thereof, thereby being sterilized.

The resin vessel 2, which is irradiated with the electron beam and hence sterilized during the passing through the interior of the irradiating chamber section 20, is rotated and conveyed while being supported by the bottle support unit 18 and then conveyed into the adjacent carry-out chamber section 22 from the irradiation chamber section 20. Within the carry-out chamber section 22, the carry-out wheel 34 is disposed, and the resin vessel 2, in which the lower side portion of the flange 2*b* is supported by the bottle support unit 18, is transferred to the gripper 36 of the carry-out wheel 34 at the transferring position B and the upper side portion of the flange 2*b* is then gripped. The resin vessel 2 rotated and conveyed while being held by the gripper 36 of the carry-out wheel 34 is then transferred to the supply wheel 39 disposed on the inlet side of the subsequent chamber (i.e., chamber 37 in the filling zone F).

The resin vessel 2 rotated and conveyed while being held by a vessel holding unit, not shown, of the support wheel 39 is supplied to the filler 112 and then held by the gripper 128. The filling nozzle 132 is then inserted into the resin vessel 2 and starts the filling operation at the predetermined position (filling starting position C). The filling operation is continued during the rotation and movement in the filling areas C-D, and as the filled amount increases, and in the rear side period in the filling areas C-D, the resin vessel 2 reaches to the position at which the voltage-apply type ionizer 134 is disposed outside the resin vessel conveying path, and at this position, the resin vessel 2 is emitted with the ions from the ionizer 134. In the present embodiment, when the electron beam irradiator 16 irradiates the resin vessel 2 with the electron beam, the earth electrode 90 is inserted, and in addition, by the emission of the ion from the ionizer 134, the charges remaining inside the wall section of the resin vessel 2 can be eliminated.

In this embodiment, since the electrons, i.e., negative charges, remain in the interior of the wall section of the resin vessel 2 by the sterilization due to the electron beam irradiation in the sterilizing zone S, the ionizer 134 emits, with the negative charges of the same polarity, to the outer surface of the resin vessel 2. If the negative charges remain in the interior of the wall section of the resin vessel 2, there creates a state in which the positive charges are on the outer surface and inner surface (inside wall section of the resin vessel 2) of the resin vessel 2. Under this state, if the negative ion emission is performed from the outer surface side of the resin vessel 2, the positively charged ions on the outer surface of the resin vessel 2 is neutralized, and then, the negatively charged ions float on the outer surface side thereof. As a result, a large amount of negative charges exists on the outer surface side of the resin vessel 2 and the interior of the wall section thereof.

Furthermore, an ion path or route connecting the ionizer 134 and the filling nozzle 132 is formed via the filling liquid L filling the resin vessel 2 and the liquid column La flowing downward from the filling nozzle 132, so that the ions having positive charges in the filling liquid L are attracted to the inner surface side of the resin vessel 2 and, on the other hand, the ions having negative charges in the filling liquid L flow to the ionizer 134 side via the liquid column La in the liquid flow and the filling nozzle 132, thus a large amount of ions having positive charges exist in the filling liquid L.

According to the processes mentioned above, at a time when the negative ion emission from the ionizer 134 has finished, a large amount of ions having negative charges exists on the outer surface side of the resin vessel 2, and the ions also having negative charges exists in the interior of the wall section thereof. According to such existence of the negatively charged ions, the ions having positive charges in the filling liquid L are attracted to inner surface side of the resin vessel 2, and hence, the negative charges remaining in the interior of the wall section of the resin vessel 2 are neutralized.

Furthermore, the ion neutralization reaction is more easily achieved in an atmosphere including much water content than in a dried condition, and as time elapses thereafter, the ions having positive charges in the filling liquid L and the negative charges remaining inside the wall section of the resin vessel 2 are mutually attracted to each other, thereby being neutralized.

As mentioned above, by generating, in the filling liquid to fill the interior of the resin vessel 2, a large amount of ions carrying positive charges which have a polarity reverse to that of the negative charges remaining in the interior of the wall section of the resin vessel 2, the neutralization reaction is more promoted in water than in atmosphere, and by utilizing this nature, the static elimination can be more effectively performed in the water than performed in the atmosphere by the ion emission. Moreover, since a large amount of ions having positive charges exists in the filling liquid L, the reaction continues even after the emission by the ionizer, and hence, the negative charges remaining in the interior of the wall section of the resin vessel 2 can be largely eliminated.

Further, in this embodiment, although the filling nozzle 132 is connected to the earth 138 on the ionizer side 134 to thereby flow the negative ions on the ionizer side 134, it is not always necessary to be connected to the ionizer side 134, and the filling nozzle 132 may be earthed independently from the ionizer 134.

Furthermore, in the above-described embodiment, although the voltage-applied type ionizer 134 is arranged on the outer peripheral side of the vessel conveying path by the filler 112, it is not always necessary to perform the ion emission during the filling process by the filler 112, and the ionizer may be disposed so as to perform the ion emission at the other portions. That is, in a second embodiment, an ionizer 234 is arranged outside of the vessel conveying path formed by the intermediate wheel 114 acting commonly as the discharge wheel from the filler 112 and a supply wheel to the capper 116.

Figure 4:
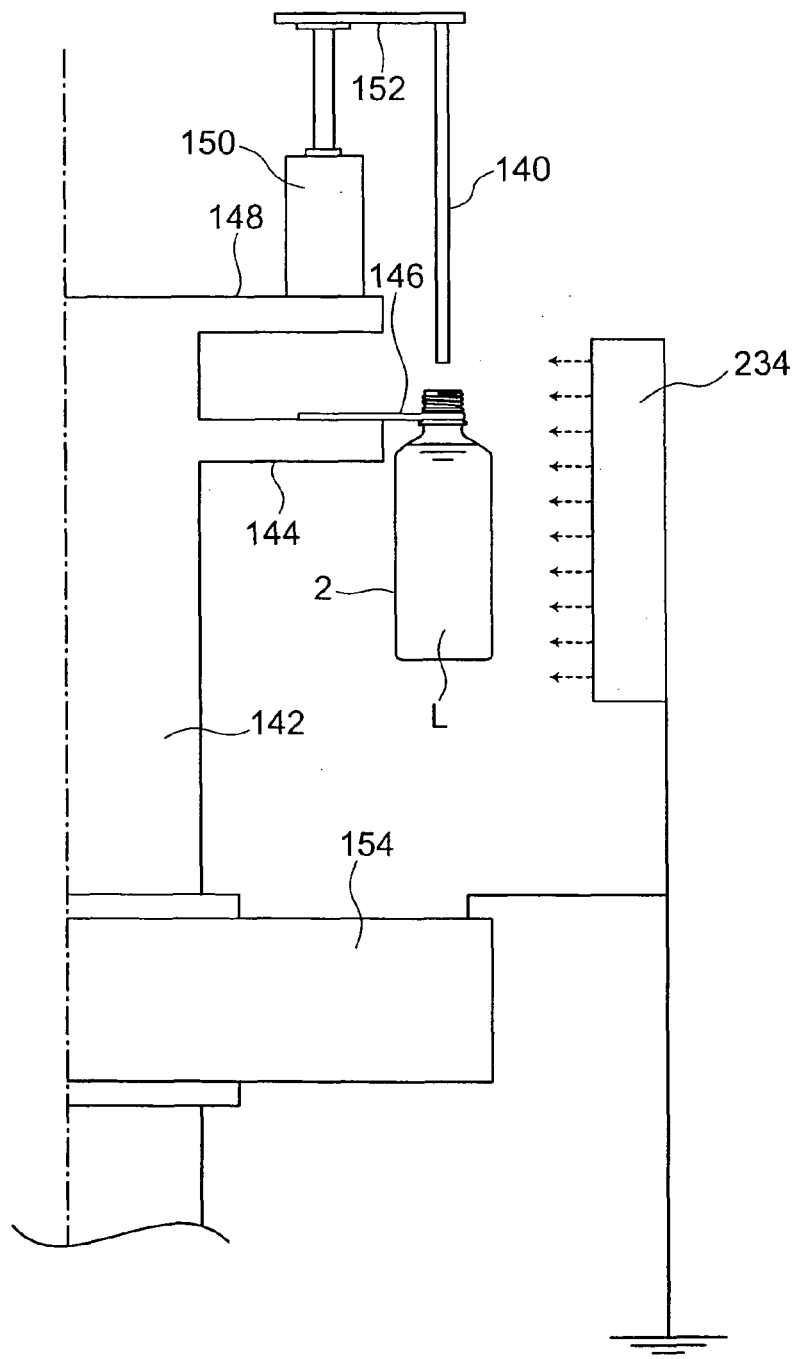
FIG. 4 is a vertical sectional view of an intermediate wheel disposed between the filler and a capper of the sterilizing and filling apparatus, which concerns a second embodiment of the present invention.

On the other hand, an electrode rod (earth electrode recited in claim 3) 140 to be inserted into the filling liquid L filled into the resin vessel 2 is provided for the intermediate wheel 114, as shown in FIG. 4, which supplies the resin vessel 2 taken out from the filler 112 to the capper 116.

The intermediate wheel 114 includes a first rotary wheel 114 around the outer peripheral portion of a vertically standing rotating shaft 142, being the center of rotation of the rotary wheel 144, and a plurality of grippers 146 holding the resin vessels 2, respectively, are disposed to the outer peripheral portion of the first rotary wheel 144 at an equal interval in the circumferential direction thereof.

Furthermore, a second rotary wheel 148 is located above the first rotary wheel 144, and a plurality of electrode rods 140 are provided in a manner such that each electrode rod 140 corresponds to each of the resin vessels 2, in the vertical alignment, held by the gripper 146. Each electrode rod 140 is fixed in a manner directed vertically downward, through a horizontal mount plate 152, to an elevating cylinder 150 fixed to the second rotary wheel 148 in a manner directed upward so as to be moved up and down in accordance with the actuation of the elevating cylinder 150.

The electrode rod 140 is operatively connected to the ionizer 234 side via the horizontal mount plate 152, the elevating cylinder 150, the second rotary plate 148, the upright rotating shaft 142, a fixing base 154 and so on, which are all made of conductive metal materials, whereby when the electrode rod 140 is inserted into the filling liquid L filled in the resin vessel 2, the ion flow path is formed from the electrode rod 140 to the ionizer 234 through the filling liquid L.

According to the structure of the second embodiment mentioned above, the voltage-applied type ionizer 234 emits to the outer peripheral surface of the resin vessel 2 with the negative ions in the state that the electrode rod 140 is lowered to be inserted into the filling liquid L by the operation of the elevating cylinder 150. In the interior of the wall section of the resin vessel 2, the negative charges remain, and there are positively charged ions on the outer and inner surfaces thereof. Accordingly, the emission of the negative ions from the ionizer 234 from the outer surface side of the resin vessel 2 neutralizes the ions having the positive charges adhering on the outer surface side thereof. Furthermore, the ions having the positive charges in the filling liquid L are attracted to the inner surface side of the resin vessel 2, and the negative ions in the filling liquid L flows outward through a circuit from the electrode rod 140 to the ionizer 234. Thus, according to this embodiment, the sterilization of the resin vessel 2 is performed by the electron beam irradiation, so that the negative charges remaining in the interior of the wall section of the resin vessel 2 can be largely eliminated.

In the respective embodiments described above, the voltage-applied type ionizers 134 and 234 are disposed outside of the conveying path by the filler 112 or outside of the discharge wheel (intermediate wheel 114) from the filler 112, and the outer surface of the resin vessel 2 which is filled with the liquid L is emitted with the negative ions to thereby neutralize the negative charges remaining inside the wall section of the resin vessel 2. However, it is not always necessary to emit to the resin vessel 2 which is filled with the liquid L with the ions, and for example, the ion emission may be performed from the outside of the resin vessel to which cleaning liquid is blown by a rinser, and in such case, the charge remaining inside the wall section will be likely eliminated.

Figure 5:
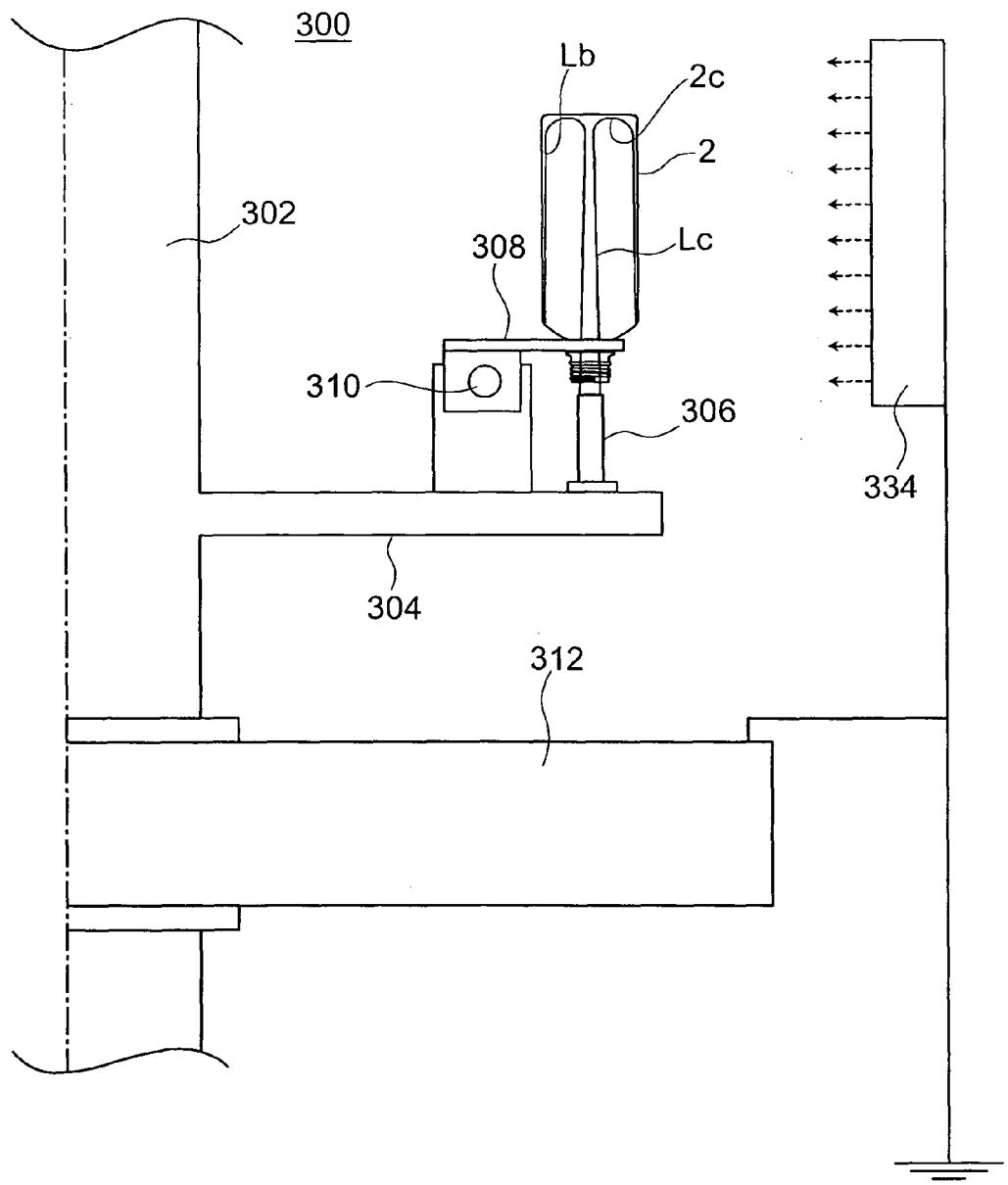
FIG. 5 is a vertical sectional view showing a state in which a structure for performing static charge elimination of a resin vessel is provided for a rinser, which concerns a third embodiment of the present invention.

FIG. 5 represents a third embodiment in which a voltage-applied type ionizer 334 is disposed outside a rinser 300. The rinser 300 of this embodiment is equipped with a plurality of cleaning nozzles 306 to the outer peripheral portion of the rotary wheel 304 mounted to the outer peripheral surface of the central rotating shaft 302 at an equal interval in the circumferential direction of the rotary wheel 304.

Bottle grippers 308 are arranged at portions radially inward of the cleaning nozzles 306, respectively. These bottle grippers 308 are pivotal around horizontally arranged fulcrum pins 310, respectively, to be reciprocally movable between a position (i.e., position shown in FIG. 5) at which the mouth portion of the resin vessel 2 held in an inverted attitude faces a drain port of the cleaning nozzle 306 and a position offset from the cleaning nozzle 306. Each of the cleaning nozzles 306 is grounded by being connected to the voltage-applied type ionizer 334 side via conductive metal members such as the rotary wheel 304, the upright rotating shaft 302, to which the rotary wheel 304 is mounted, and the base 312 supporting the rotating shaft to be rotatable.

In this embodiment, although the liquid L does not fill the resin vessel 2 as in the former embodiments, the outer surface of the resin vessel 2 is contacted with the negative ions from the ionizer 334 during the cleaning process in which the cleaning liquid is jetted toward the inner side bottom surface 2c of the resin vessel 2 from the cleaning nozzle 306, thereby achieving substantially the same effects and functions as those attained by the former embodiments.

During the cleaning process in which the cleaning liquid is jetted from the cleaning nozzle 306, the cleaning liquid jetted from the cleaning nozzle 306 to the bottom surface 2c of the resin vessel 2 flows downward along the inside surface of the resin vessel 2. In this state, if the ion emission is performed, the cleaning nozzle 306 and the ionizer 334 become conductive through the liquid column Lc flowing to the bottom surface 2c of the resin vessel 2, and hence, the positively charged ions flow to the earth side of the ionizer 334 via the cleaning nozzle 306, the rotary wheel 304, the rotating shaft 302 and the base 312, as mentioned above, and the positively charged ions existing in the cleaning liquid Lb are attracted to the inner surface side of the resin vessel 2.

As mentioned above, even in the case where the resin vessel 2 is not filled with the liquid, the cleaning nozzle 306 can be grounded, while performing the rinsing process, through the liquid column Lc of the cleaning liquid jetted from the cleaning nozzle 306 and the cleaning liquid Lb flowing along the inner surface of the resin vessel 2, thereby attaining substantially the same effects as those attained by the former embodiment.

What is claimed is:

1. A method of eliminating static charge from a resin vessel by using an apparatus including a liquid supply unit for supplying a liquid into a resin vessel and a charge applying unit for applying charge to an outer surface of the resin vessel, wherein, by applying charge having a same polarity as that of charge remaining in an interior of a wall section of the resin vessel, while supplying the liquid into the resin vessel, ion carrying charge having a polarity reverse to that of the charge remaining in an interior of the wall section of the resin vessel is attracted to an inner surface of the resin vessel.

2. The method of eliminating static charge from a resin vessel according to claim 1, wherein the charge applying unit is a device for emitting to the outer surface of the resin vessel with ions.

3. An apparatus for eliminating static charge from a resin vessel comprising a liquid supply unit for supplying a liquid into a resin vessel and a charge applying unit for applying charge to an outer surface of the resin vessel which is filled with the liquid by the liquid supply unit, wherein charge having a same polarity as that of charge remaining in an interior of a wall section of the resin vessel is applied to the outer surface of the resin vessel by the charge applying unit during the supply of the liquid into the resin vessel by the liquid supply unit.

4. The apparatus for eliminating static charge from a resin vessel according to claim 3, wherein the charge applying unit is a device for emitting to the outer surface of the resin vessel with ions.

5. In a method of sterilizing and filling a resin vessel in which a resin vessel is sterilized by irradiation with an electron beam and a filling nozzle fills the resin vessel with a liquid, the improvement comprises providing a negative charge applying unit for applying a charge on an outer surface of the vessel which is the same polarity as a charge remaining in the interior of a wall section of the resin vessel during the liquid filling step.

6. The method of sterilizing and filling a resin vessel according to claim 5, wherein the negative charge applying unit is a device for emitting ions to the outer surface of the resin vessel.

7. A resin vessel sterilizing and filling system, comprising: an electron beam irradiator for irradiating a conveyed resin vessel with an electron beam and thereby sterilizing the resin vessel; a filling unit comprising a filling nozzle for discharging a liquid into the resin vessel through an upper portion of a mouth portion of the resin vessel which has been irradiated with the electron beam; a capping unit for applying a cap on the resin vessel after it is filled with the liquid and a negative charge applying unit for applying a charge onto an outer surface of the resin vessel, wherein the negative charge applying unit applies a charge onto the outer surface of the vessel which is the same polarity as a charge remaining in the interior of a wall section of the resin vessel during the liquid filling of the resin vessel.

8. The resin vessel sterilizing and filling system according to claim 7, wherein the negative charge applying unit is a device for emitting ions to the outer surface of the resin vessel.

* * * * *